United States Patent [19]
Klingenstein

[11] Patent Number: 6,149,581
[45] Date of Patent: Nov. 21, 2000

[54] DEVICE AND METHOD FOR ACCESS TO THE COLON AND SMALL BOWEL OF A PATIENT

[76] Inventor: Ralph James Klingenstein, 151 Tremont St., Apt. 23E, Boston, Mass. 02111

[21] Appl. No.: 08/874,991

[22] Filed: Jun. 12, 1997

[51] Int. Cl.⁷ .................................................. A61B 1/04
[52] U.S. Cl. ........................................ 600/114; 606/197
[58] Field of Search ............................ 600/114, 115, 600/116, 117, 371, 458; 606/108, 151, 197

[56] References Cited

U.S. PATENT DOCUMENTS

| | | | |
|---|---|---|---|
| 2,767,705 | 10/1956 | Moore ................................ | 600/114 X |
| 2,974,666 | 3/1961 | Coumbis et al. .................. | 606/197 X |
| 3,913,565 | 10/1975 | Kawahara ........................... | 600/114 X |
| 4,167,939 | 9/1979 | Storz ..................................... | 600/114 |
| 4,471,782 | 9/1984 | Shuffield ............................. | 606/197 |
| 4,750,477 | 6/1988 | Wardle . | |
| 4,762,120 | 8/1988 | Hussein . | |
| 4,773,394 | 9/1988 | Reichstein et al. ................. | 600/114 |
| 4,776,845 | 10/1988 | Davis ................................. | 600/114 X |
| 4,841,949 | 6/1989 | Shimizu et al. . | |
| 4,957,486 | 9/1990 | Davis . | |
| 4,971,033 | 11/1990 | Ehlers . | |
| 5,292,802 | 3/1994 | Rhee et al. . | |
| 5,312,343 | 5/1994 | Krog et al. ......................... | 606/197 X |
| 5,332,070 | 7/1994 | Goodman et al. .................. | 606/197 X |
| 5,353,783 | 10/1994 | Nakao et al. . | |
| 5,423,830 | 6/1995 | Schneebauh et al. . | |
| 5,489,256 | 2/1996 | Adair . | |

FOREIGN PATENT DOCUMENTS

| | | |
|---|---|---|
| 0 677 272 A1 | 10/1995 | European Pat. Off. . |
| 0 747 069 A2 | 12/1996 | European Pat. Off. . |
| WO 94/05200 | 3/1994 | WIPO . |
| WO 96/00517 | 1/1996 | WIPO . |

OTHER PUBLICATIONS

Wilson–Cook Medical Inc., Esophageal/Gastric/Colonic, Decompression Tubes 7C–1, 14FR Colon Decompression Set.

Wilson–Cook Medical Inc., Esophageal/Gastric/Colonic, Decompression Tubes 7C–2, Marcon Colon Decompression Sets.

Wilson–Cook Medical Inc., Esophageal/Gastric/Colonic, Decompression Tubes 7C–3, Brodmerkel Colon Decompression Sets.

Martin et al., "Therapeutic Colonoscopy in the Treatment of Colonic Pseudo-obstruction" vol. 54 *The American Surgeon*, pp. 519–521 (1988).

*Primary Examiner*—Beverly M. Flanagan
*Attorney, Agent, or Firm*—Testa, Hurwitz & Thibeault, LLP

[57] ABSTRACT

Provided are devices and methods to provide access to the colon and small bowel of a patient. The devices comprise a tubular member that is releasably attachable to a colonoscope for insertion into the colon. The devices are useful for treating and monitoring colorectal diseases, and diseases of the small bowel.

25 Claims, 4 Drawing Sheets

DEVICE AND METHOD FOR ACCESS TO THE COLON AND SMALL BOWEL OF A PATIENT

FIELD OF THE INVENTION

The invention relates to cecal access devices and methods which provide access to a patient's colon, cecum, or ileum for the removal or introduction of material over a period of time.

BACKGROUND OF THE INVENTION

Figure 1:
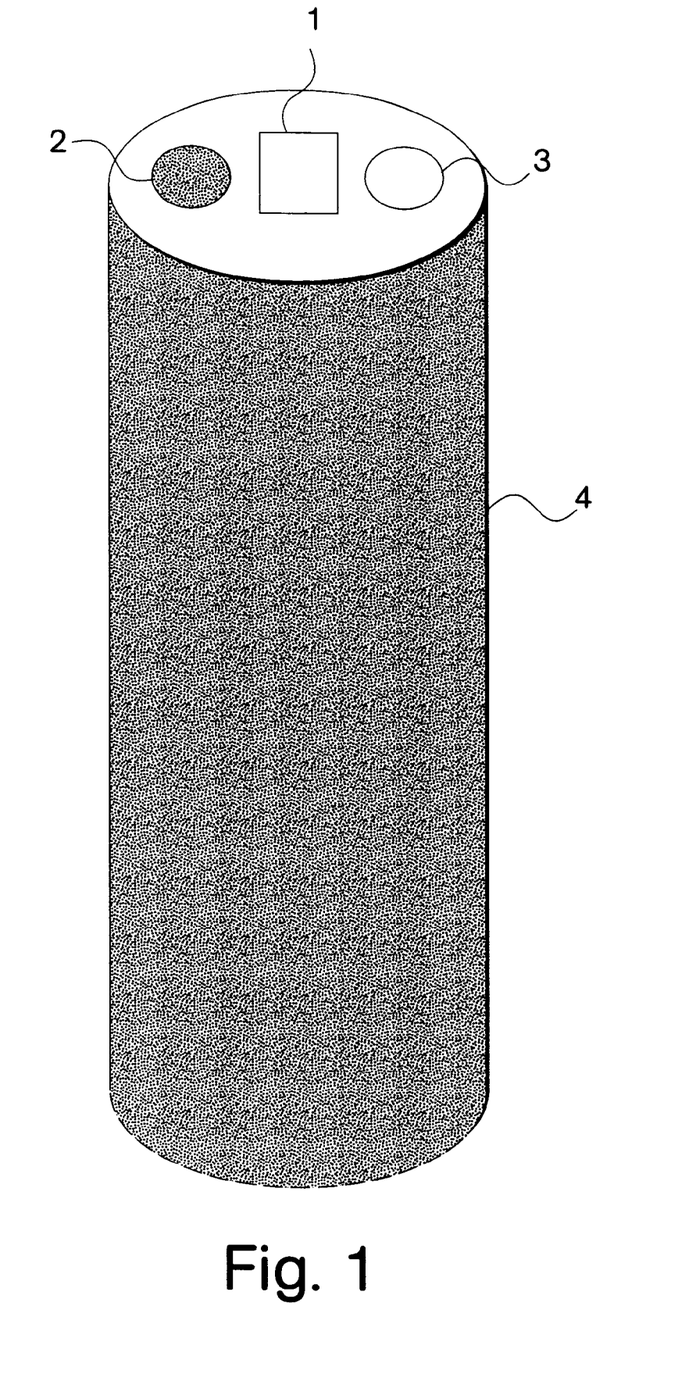

The adult colon is approximately 6 feet long and extends from the cecum to the rectum via the ascending, transverse, descending and sigmoid colons. Lesions resulting from a number of different disease conditions, such as colon cancer, ulcerative colitis and other inflammatory bowel diseases, can arise at any position along the length of the colon. Diagnosis of these different conditions typically involves visual examination of the colon using, for example, a colonoscope. A typical colonoscope comprises, at its proximal end, a light source, a video chip, and a suction channel. These elements are all in communication with the distal end of the colonoscope via wires and channels housed within a flexible tube. The proximal end of a typical colonoscope is shown in FIG. 1. The proximal end is inserted into a patient's rectum and can be maneuvered along the length of the colon. A colonoscope can be inserted far enough into a patients colon for the proximal end of the colonoscope to enter the patient's cecum. The tip of the colonoscope can also be maneuvered through the ileo-cecal valve into the terminal ileum. Colonoscopes provide a visual image only of the region of the colon that is immediately proximal to the light source and video chip. Lesions in a patient's colon typically are identified by progressive and painstaking visual examination of the entire colon. Various attachments to a colonoscope allow small surgical procedures, such as tissue biopsies, to be carried out during a colonoscopic examination. For example, U.S. Pat. No. 5,423,830 reports a polyp retrieval instrument assembly attached to a colonoscope.

Colonoscopes have also been used for therapeutic purposes, for example to relieve the cecal pressure buildup associated with colonic pseudo-obstruction or Ogilvie's syndrome. Martin, et al., *The American Surgeon*, 54: 519–521 (1988). Patients suffering from Ogilvie's syndrome typically present an acutely distended colon, and a distended cecum in particular. These symptoms result from an accumulation of gas in the lumen of the colon. Insertion of the proximal end of a colonoscope into the cecal lumen relieves the pressure by removing gas through the suction channel in the colonoscope.

Colonoscopies are typically transient procedures. Colonoscopes are complex and expensive devices, and they are not placed in a patient's colon for any length of time beyond that required for visual observation, tissue biopsy or decompression. As a result, patients suffering from Ogilvie's syndrome often require a series of decompressing colonoscopies due to recurring accumulation of gas in the lumen of the colon. Martin, et al., *The American Surgeon*, 54: 519–521 (1988). These result in additional expense and risk to the patient.

A colonoscope provides visual information for only a small region of the colon at any given time. However, a single colonoscopy is often not sufficient to identify the source of colorectal bleeding which is typically sporadic and in many cases would be best located by observing the entire colon over a period of time.

There is therefore a need in the art for simple devices and methods for prolonged access to a patient's colon. Such devices and methods are provided by the present invention.

SUMMARY OF THE INVENTION

The present invention provides colonic access devices and methods for access to a patient's colon, cecum, or ileum. In general, a device according to the invention is designed to be placed in the colon of a patient for a prolonged period of time, ranging from several hours to several days. A device according to the invention comprises a tubular member having a proximal end and a distal end. As used herein, the proximal end of a device or a positioning probe is the end that is inserted into the colon of a patient. The distal end is the end that remains closest to the rectum of a patient. When placed in the colon of a patient, the proximal end of the tubular member is inserted toward the cecum, and the distal end of the tubular member remains at the rectal end of the colon. The device further comprises a tether for releasable association of the tubular member with a positioning probe. For purposes of the invention, a positioning probe is an instrument that is inserted, via the rectum, to a desired position within the colon of a patient. An example of a positioning probe is an endoscope, such as a colonoscope. A feature of the invention is that the tether is designed to permit release of the colonic access device from the positioning probe once it is at a desired location within the colon. Thus a colonic access device can be placed such that its proximal end is at a chosen position along the length of the colon, cecum, or ileum of a patient. In methods of the invention, the positioning probe is used to place a colonic access device at a precise location in the colon. The device is then released from the positioning probe which is subsequently removed from the colon.

When the proximal end of the tubular member is placed in the cecal lumen of a patient, the distal end is connectable to a sampling or monitoring apparatus via the rectum. For purposes of the invention, the shape of the tubular member is generally cylindrical, but may be flattened or shaped to fit the contour of a colonoscope.

In a preferred embodiment, the tubular member defines a hollow cavity with an opening at a proximal end and an opening at a distal end. Such an embodiment is useful for introducing material to or removing material from the colonic lumen or its epithelial lining via the cavity. This embodiment is useful, for example, to relieve cecal pressure associated with gas accumulation in, for example, Ogilvie's syndrome. For use in Ogilvie's syndrome, the device is placed such that the proximal end is in, or adjacent to, the cecal lumen and the distal end remains outside of the patient's body. Cecal decompression occurs as gases move through the proximal opening into the cavity and out the distal opening. In a preferred embodiment, suction is used to remove the excess gas from the cecum via the colonic access device.

In a most preferred embodiment, the tubular member comprises two openings. A first opening is located adjacent the proximal end of the tubular member, and a second opening is located adjacent the distal end of the tubular member. Material, for example, colonic effluent, in the proximal end of the colon is sampled through the first opening, and material in the distal end of the colon is sampled through the second opening. The sampled material is then tested for blood or other disease indicators. Also in a preferred embodiment, the tubular member comprises a plurality of openings, each connected to an independent channel. The openings communicate between a channel forming a hollow tube within the cavity of the device, and the exterior of the device. Each channel runs from the opening to the distal end of the tubular member. Each channel may be connected to a sampling or monitoring apparatus. This embodiment is useful, for example, to locate a lesion in a patient suffering from colorectal bleeding.

Devices of the invention are also useful to deliver pharmaceutical compositions or contrasting agents to specific portions of the colon, cecum, or ileum, via openings in the tubular member. In a preferred embodiment, the device is used to deliver a pharmaceutical composition to the colon via the cecum. The pharmaceutical composition is introduced into the cecum, and the composition subsequently travels from the cecum through the colon. In alternative embodiments, the cecal access device further comprises an inflatable member, such as a balloon, to prevent the pharmaceutical compositions or contrasting agents from spreading along the length of the colon. In one embodiment, the inflatable member is located immediately distal to the opening through which a pharmaceutical composition or contrasting agent is delivered. Administration of the pharmaceutical composition or contrasting agent after inflation of the inflatable member results in a highly localized accumulation of the administered product. In a further embodiment, a device according to the invention is useful to detect the presence of lesions such as leiomyomas, or fistulas related to Crohn's disease in the distal to mid small bowel. A device of the invention is also useful for delivery of a stent to the distal small bowel. The proximal tip of a device is placed, using a colonoscope for example, in the distal portion of the ileum or small bowel. Radiologic contrasting agent is introduced into the small bowel via the lumen of the device. The small bowel is visualized by X-ray analysis to identify any lesions in the small bowel. Lesions may include fistulas resulting from, for example, Crohn's disease, strictures, neoplasms, or diverticula, for example Meckel's diverticulum.

Devices of the invention are also useful to monitor colorectal pressure. In a preferred embodiment, a device of the invention comprises a plurality of pressure sensors along the length of the tubular member.

In a preferred embodiment the releasable association of the colonic access device with the positioning probe involves a string or a cord or a wire or an equivalent thereof. The device comprises a bore at the proximal end of the tubular member through which the string or wire is inserted.

Numerous additional features and advantages of the invention will become apparent upon consideration of the following detailed description thereof.

DETAILED DESCRIPTION OF THE INVENTION

DESCRIPTION OF THE DRAWINGS

FIG. 1 shows the proximal end of a typical colonoscope. The Figure shows a light source 1, a video chip 2, a suction channel 3, and the flexible tube 4 which houses the wires and channel connected to the light source and video chip, and suction channel, respectively. The dotted line indicates that the flexible tube extends beyond the scope of the drawing, and that only the proximal end of the colonoscope is represented.

FIG. 2B is a side view.

FIG. 3B shows the inner surface of the proximal end of FIG. 3A. The inner surface (shadowed in the drawing) is contoured to fit the shape of the proximal end of a colonoscope. The Figure shows tether 8 for releasable association of the device with the colonoscope. The dotted lines indicate that the tubular member extends towards its distal end beyond the scope of the drawing. Only the proximal end of the tubular member is represented in FIGS. 3A and B.

The present invention provides devices and methods that allow access to a patient's colon, cecum, and ileum. In general, a device according to the invention comprises a tubular member having a proximal end and a distal end. The device further comprises a tether for releasable association of the tubular member with a positioning probe, such as a colonoscope. In a preferred embodiment, the positioning probe is used to place the proximal end of the tubular member at a desired location within the colon of a patient. The device is subsequently released from the probe which is then withdrawn, leaving the proximal end of the tubular member positioned in the lumen of the colon. In a preferred embodiment, the distal end of the tubular member is connected, via the rectum, to additional instruments outside the body of the patient. In a preferred embodiment, the positioning probe is a long flexible tool with a proximal end that is inserted into the colon of a patient via the rectum. The probe is progressively inserted into the colon, and the progress of its proximal end typically is monitored visually. The proximal end of a typical positioning probe comprises a light source and a video chip. An example of a positioning probe is a colonoscope, the proximal end of which is shown in FIG. 1. Devices and methods of the invention are also useful with other positioning probes which can be inserted into the colon of a patient.

Once placed in the colon of a patient, a device according to the invention can be left in position for several hours to several days, depending on the application. Different embodiments of the invention are useful to treat or monitor a number of conditions, including colonic pseudo-obstruction or Ogilvie's syndrome, intestinal bleeding, and other intestinal disorders. Devices and methods of the invention avoid the need for multiple colonoscopies, which are often required to treat, for example, Ogilvie's syndrome, or to identify the source of intestinal bleeding. In addition, embodiments of the present invention can be used to monitor the entire length of the colon over a period of time. Devices and methods of the invention are also useful to introduce material into the distal and mid small bowel. The invention also provides new approaches to identifying and treating lesions in the small bowel of a patient.

Figure 2A:
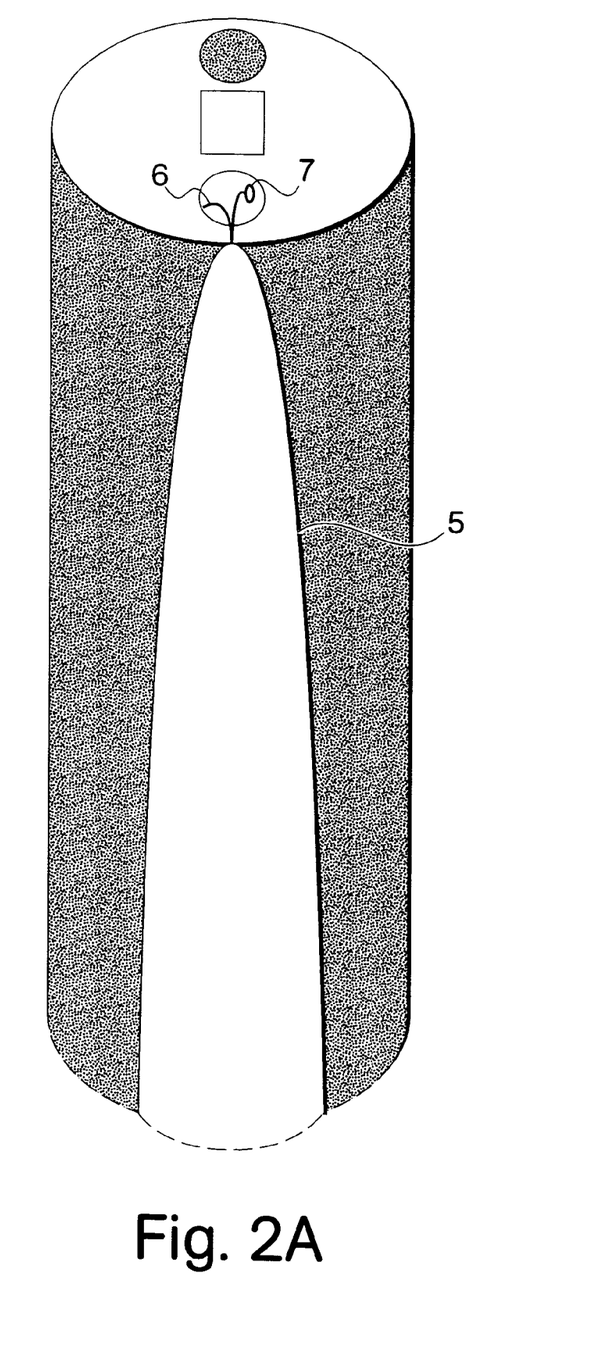
FIGS. 2A and 2B show a device of the invention in association with the proximal end of a colonoscope. The figure shows the proximal end 5 of the tubular member of a device according to the invention. In the embodiment that is illustrated, the tubular member is tapered at its proximal end. The tubular member is also flattened and contoured to fit the shape of the colonoscope. The device is releasably associated with the colonoscope via cord 6. The device further comprises catch 7, which can be securely grasped with a tool such as a forceps during removal of the colonoscope according to methods of the invention.
Figure 2B:
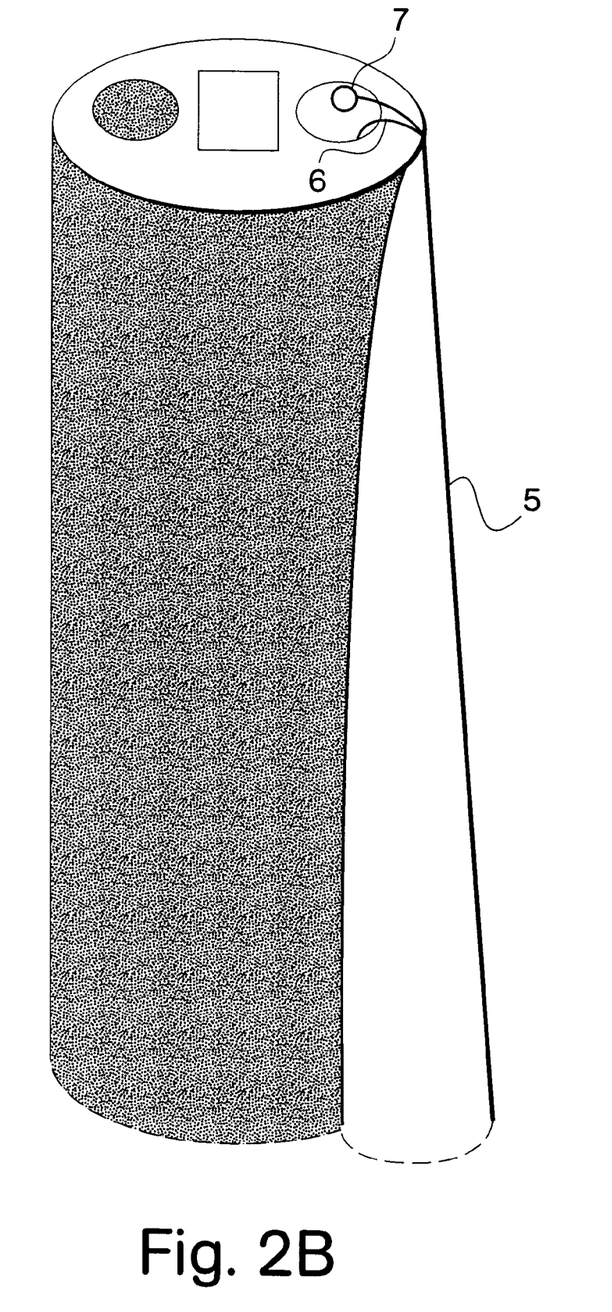
Figure 3A:
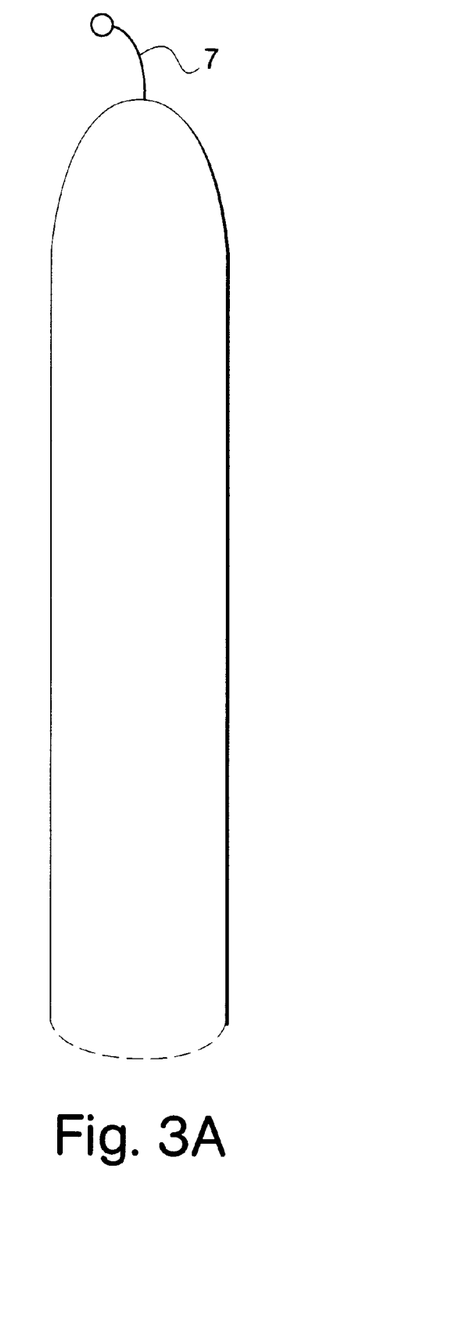
FIG. 3A shows the outer surface of the proximal end of the tubular member of a device according to one embodiment of the invention. Catch 7 is shown at the tip of the proximal end.
Figure 3B:
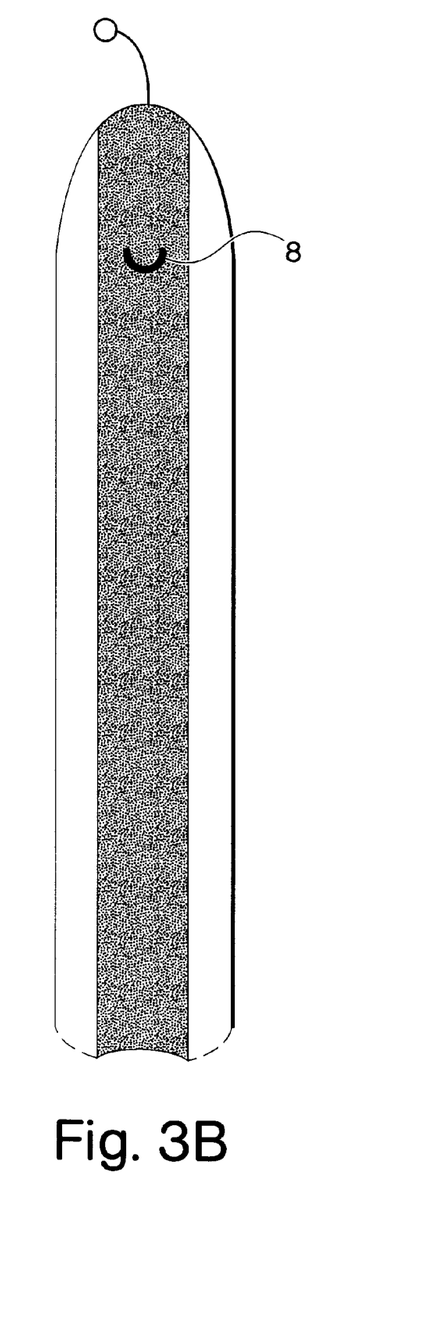

In a preferred embodiment, the tubular member of the invention is constructed from a flexible, biocompatible material, such as plastic, rubber, or a synthetic compound, such as a styrene-butadiene copolymer. In a more preferred embodiment, the proximal end of the tubular member is stiffer than the rest of the tubular member. In general, the tubular member is sufficiently flexible to adapt to the shapes of bends along the length of the colon, without imposing physical stress on the walls of the colon. However, a stiffer proximal end is useful for maintaining the position of the device in the colon. In a preferred embodiment, the stiffer section comprises approximately the proximal 30 cm of the tubular member. Also in a preferred embodiment, the surface of the tubular member is covered with a layer of soft material to prevent damage to, or erosion of the epithelial lining of the colon. In a preferred embodiment the layer of soft material is about 1 to 5 mm thick. In a more preferred embodiment the layer is about 2 mm thick. The length of the tubular member preferably extends at least the distance from the cecum to the rectum and more preferably from the small bowel to the rectum of an adult patient. The tubular member is from about 5 to about 8 feet long, and preferably about six feet long. The diameter of the tubular member preferably is greater than approximately 0.1 cm and smaller than approximately 5.0 cm, and more preferably is greater than approximately 0.5 cm and smaller than approximately 2.0 cm, and most preferably is approximately 1.5 cm. However, the skilled artisan will appreciate that tubular members of different diameters will be useful for different applications of the invention. In a preferred embodiment, the proximal end of the device is tapered to provide a blunt tip so as to minimize the risk of damaging the lining of the colon during insertion of the device. In a most preferred embodiment, the proximal end of the device is also be shaped to fit the contour of the positioning probe, thus reducing the combined cross-sectional area of the positioning probe and attached colonic access device. Such a reduced cross-sectional area also is desirable to minimize the risk of injury to the colon during insertion of the device in association with the positioning probe. FIG. 2 shows an embodiment of the invention wherein the proximal end of the tubular member is tapered and shaped to conform to the shape of the colonoscope. In an alternative embodiment, the entire length of the tubular member is contoured to fit the shape of the colonoscope.

In a preferred embodiment, a device of the invention comprises a tubular member defining an internal hollow cavity. In a most preferred embodiment, walls of the tubular member define an opening at the distal end and an opening at the proximal end of the tubular member. The internal cavity is in fluid communication with the lumen of the colon, cecum or ileum via the opening at the proximal end when the device is placed inside a patient. The internal cavity is in fluid communication with the space outside the patient's body via the opening at the distal end. This embodiment is useful to vent gases from the lumen of the colon to the space outside the body of the patient. In a most preferred embodiment, excess gases are removed from the lumen of the colon using suction generated by connecting the distal opening to a vacuum. When the proximal end is placed in the cecum, the device is useful for cecal decompression over an extended period of time, thus providing relief for patients suffering from Ogilvie's syndrome. In a more preferred embodiment, the cecal decompression is intermittent (generated by intermittent suction) thus removing gases when they accumulate. In a preferred embodiment, the frequency of cecal decompression is regulated by the skilled practitioner and is a function of the degree of cecal distension. Cecal distension is monitored by serial X-ray analysis. The cecum is visualized by X-ray imaging in the absence of radiologic contrast agent, and cecum size changes over time are observed by taking a series of X-ray images. In an alternative embodiment the device is responsive to the pressure in the cecum and removes excess gas when the pressure rises above a predetermined threshold. In one embodiment a pressure sensor located at the proximal end of the device relays information to a pressure readout device.

The practitioner then decompresses the cecum when the pressure rises above normal. Alternatively, the pressure sensor relays information to a regulator which automatically decompresses the cecum when the pressure reaches a predetermined level. Alternative techniques for sensing and monitoring the cecal pressure are also contemplated by the invention. In an alternative embodiment the decompression is continuous, however suction should be carefully regulated to prevent the cecal wall from being aspirated into the device. The opening at the proximal end may be located at the tip of the proximal end, or on a side of the tubular member at a distance from the tip of the proximal end, providing that the distance is small enough to allow cecal gases to vent through the opening. The opening may be a single aperture, or may comprise a series of apertures. In a preferred embodiment, a number of apertures are distributed around the circumference of the tubular member at its proximal end. This reduces the problems caused by blockage of a single aperture by fecal material, or by direct contact of the lining of the colon with the aperture.

Also in a preferred embodiment the device is useful to decompress the colon at any position between the cecum and the rectum. The device is placed such that an opening at the proximal end is in communication with the region of the colon in need of decompression. Alternatively, the wall of the tubular member defines a plurality of apertures located at defined positions along the length of the tubular member. When the proximal end of this device is placed in the cecum, each one of a plurality of regions of the colon is in communication with the internal cavity of the tubular member via one of the plurality of apertures. A device with a plurality of apertures, each in communication with the internal cavity, is useful for decompressing the entire colon.

In another embodiment, the hollow cavity of a colonic access device is subdivided into a plurality of separate sampling channels. Each sampling channel is connected to a separate sampling opening at a known location on the tubular member, and runs the length of the tubular member connecting the sampling opening to the distal end. At the distal end, each sampling channel is connected to a collection device or apparatus, for example a test tube. In a preferred embodiment, the sampling openings are distributed along the length of the tubular member, such that each opening is in communication with a different section of the colon when the device is placed inside a patient. In a more preferred embodiment, the device comprises a first aperture at the proximal end, and second and third apertures at the distal end. In a most preferred embodiment, the second and third apertures are located such that they are respectively about 40 cm and 20 cm proximal to the rectum when the device is located in the colon of a patient. Also in a most preferred embodiment, the device comprises a proximal aperture and a distal aperture, located such that it is about 30 cm proximal to the rectum when the device is placed in the colon of a patient. In a preferred embodiment, each sampling channel is put under vacuum to aspirate a sample from the lumen of the colon in the region surrounding the opening. In a preferred embodiment, each sampling opening comprises a number of apertures to minimize the risk of blockage as described above. A device comprising a plurality of sampling openings is useful for identifying the source of intestinal bleeding in a diseased patient. Samples are obtained through each opening at regular time intervals and monitored for the presence of blood. The presence of blood in a given sample identifies the approximate region of the colon which is bleeding. In a preferred embodiment, the colon is flushed with a lavage solution once the device is correctly placed, prior to sampling. The patient ingests a buffered solution of polyethylene glycol (Golytely for example) or an equivalent thereof, which washes out the contents of the gastrointestinal tract. The apertures of the sampling device are also flushed with a lavage solution that is injected through the sampling channels. Samples are subsequently obtained by applying intermittent suction to the sampling channels for a time sufficient to detect bleeding. Colorectal bleeding is often sporadic and samples may be taken over a period of several hours or days before any blood is detected. A device comprising multiple openings is also useful for treating Ogilvie's syndrome, providing one of the openings is in contact with the cecal lumen.

Alternatively, a device of the invention comprises a plurality of sensors, each of which is responsive to the presence of blood. Such a device is used to locate the source of gastrointestinal bleeding in a patient. The position of each sensor on the device is predetermined. When such a device is placed at a known position in the colon of a patient the approximate location of blood is provided by the response of one or more sensors. In a preferred embodiment, the device comprises one or more sensors which are sensitive to the oxidation state of blood. Such sensors are useful to distinguish between old blood and fresh blood. The above devices obviate sample collection and analysis steps in gastrointestinal blood detection.

In embodiments of the invention used for treating Ogilvie's syndrome or for monitoring intestinal bleeding, blockage of the openings by the lining of the colon can be further minimized by adapting the device to comprise extendible protrusions useful to displace the lining of the colon from the surface of the device. An extendible protrusion may comprise a rigid attachment which is extended by activating a system of wires or strings. Alternatively, an extendible protrusion may comprise an inflatable component. Other extendible protrusions are also useful to reduce blockage of the openings. In a preferred embodiment each opening is covered by a flap. When a sample is being obtained the flap is raised and acts as an extendible protrusion to displace the lining of the colon if it is in direct contact with the surface of the device around the opening. In a preferred embodiment, one end of the flap is attached to the device via a hinge and the other end is free. The flap is raised by pulling on a string. In one embodiment the string is attached to the free end, and activation of the string rotates the free end of the flap outward and away from the wall of the device. The string can be any cordlike attachment, such as a wire or synthetic cord. In an alternative embodiment the flap is opened by inflating an inflatable portion of the flap. Other mechanisms for opening the flap are also contemplated by the invention, and include magnets and mechanical wheels. In additional embodiments, the openings are recessed further to minimize blockage by the lining of the colon. In a preferred embodiment, blockage of openings can be prevented or cleared by flushing a buffered solution through the colon of a patient as described above. Also in a preferred embodiment, prior to insertion of the device the colon of a patient is cleared, using a buffered solution or other methods known in the art. In a most preferred embodiment, a patient does not ingest food while a device of the invention is in the patient's colon. This prevents blockage of openings and also minimizes the risk of the device shifting due to pressure exerted by material in the colon.

Devices according to the invention are also useful for delivering substances, such as pharmaceutical compositions or contrasting agents, to the colon or specific regions thereof. Barium or gastrografin X-ray contrast media or an equivalent thereof may be introduced into the cecum specifically to study the cecum or appendix. This feature is enhanced by having an inflatable member such as a balloon at the proximal end of the tubular member, such that inflation of the balloon at least partially occludes the lumen of the colon. According to one embodiment of the invention, medication is introduced into the cecum, and the medication then moves distally in the colon. This method is useful to expose the length of the colon to a pharmaceutical compound, for example a topical medication. In alternative embodiments, medication is instilled at one or several specific locations in the colon. Exposure to medication is thereby limited to specific regions of the colon. In preferred embodiments, medication is introduced over one or more predetermined time periods. Medication can therefore be introduced locally to treat diseases such as Crohn's disease, ulcerative colitis and other inflammatory bowel diseases which may affect limited regions or the entire length of the colon. Methods of the invention are useful for local introduction of medication in doses that are higher than could be achieved by systemic administration. Indeed, many pharmaceutical compositions, such as steroid based drugs, used to treat inflammatory bowel diseases, have undesirable side effects when administered systemically in high doses. In an alternative embodiment an inflatable member occludes the lumen of the colon distal to the site of administration of the contrasting agent or pharmaceutical composition. This occlusion temporarily prevents the administered compound from moving distally, resulting in a localized accumulation of the administered compound. Local accumulation of a contrasting agent in a predetermined region of the colon is useful to visualize the region without filling the entire colon within the contrasting agent. Local accumulation of a pharmaceutical composition is useful to treat a localized lesion in the colon without exposing the entire colon to the pharmaceutical composition. This is desirable when the pharmaceutical composition is expensive, or to further reduce any side-effects caused by the medication. The embodiments described above obviate problems associated with the systemic administration of medication, thus providing greater potency and/or minimized side effects. Examples of conditions for which such topical treatment is useful include, inter alia pseudomembranous colitis (C. difficile colitis) in the presence of a small bowel ileus, and ulcerative or Crohn's colitis (inflammatory bowel disease of the colon) not responsive to systemic administration of medications such as steroids or immunosuppressives. Useful pharmaceutical compositions include acetylcholine, metoclopramide, cisapride, naloxone for treating idiopathic intestinal pseudoobstruction, and mesalamine and leukotriene inhibitors for treating ulcerative colitis. Methods and devices of the invention are also useful for administering antisense therapeutics to specific regions of the colon. These therapeutics are useful, for example, to treat inflamed lesions. Local administration of pharmaceutical compositions, such as antisense therapeutics and anti-inflammatory drugs, is also useful following surgical resection of the colon.

In a further embodiment, methods and devices of the invention are useful in an alternative enteroclysis method referred to herein as retrograde enteroclysis. In retrograde enteroclysis material, such as a radiologic contrast agent, is delivered to the small bowel. The proximal end of a device according to the invention, attached to the proximal end of a positioning probe, for example a colonoscope, is placed in the terminal ileum through the ileo-cecal valve. The radiologic contrast agent is introduced into the terminal ileum through the lumen of the device. In a preferred embodiment, the device comprises an inflatable section at its proximal end. When inflated, this section occludes the ileo-cecal valve and prevents the contrast agent from flowing into the cecum instead of filling the ileum and small bowel. The inflated section also anchors the device in the terminal ileum. In a preferred embodiment the inflatable section comprises an inflatable ring around the entire circumference of the device, adjacent its proximal tip. In a preferred embodiment, the contrast agent is introduced only into the terminal ileum. In an alternative embodiment additional contrast agent is introduced to fill the ileum or distal small bowel. The small bowel or a portion thereof, is subsequently visualized, for example, by X-ray analysis, to detect any lesions present in the epithelial wall of the bowel. In one embodiment planar X-ray analysis is used. In an alternative embodiment, computed tomographic X-ray analysis is used. Lesions contemplated by the invention include Meckels diverticulum; other diverticula; strictures or fistulas associated with an inflammatory bowel disease such as Crohn's disease; neoplasms; and other lesions associated with bowel disease. Lesions may be more readily detected using computed tomographic X-ray analysis if they are not detected under planar X-ray analysis.

In an alternative embodiment, a device according to the invention is adapted to record pressure measurements along the length of the colon: a cecum-to-rectum tubular member with multiple pressure sensors along its length provides manometric research data useful to better classify and treat irritable bowel syndrome and diverticulosis.

Devices according to the invention are placed in the colon using a positioning probe. In a preferred embodiment, the proximal end of the tubular member comprises a tether for releasable association with the end of the probe which is inserted into the patient. The probe is then maneuvered to the desired position and the device is released. The probe is withdrawn and the device remains in the colon until treatment or monitoring is complete. The tether for releasable association of the device with the probe can take on many embodiments, but it must allow the device to be positioned in the colon along with the probe. The tether must also allow the device to be released once it is correctly positioned in the colon. In a preferred embodiment, the probe is a colonoscope, and the device is attached to the colonoscope via a wire, cord or string or an equivalent thereof. The wire may be made of metal, or plastic, or a synthetic polymer, or an equivalent thereof. In a preferred embodiment, the wire is passed serially completely through both the suction channel of the colonoscope and a bore that preferably runs from the proximal end to the distal end of the device, such that the respective proximal tips of the colonoscope and the device are proximate each other near the center of the length of the wire. In a more preferred embodiment, the bore is the internal cavity of a device, wherein the cavity has openings at both the proximal and distal ends of the device. The wire is clamped at each end, capturing the colonoscope and the device on the wire. The device is then doubled back along the colonoscope so that as the colonoscope is inserted into the into the colon, the device is carried along therewith. When the tip of the colonoscope is in the desired location in the colon, for example the cecum, the clamps and wire are removed, and the colonoscope is then removed. Also in a preferred embodiment, a wire is attached to the proximal end of the device, and passed through the suction channel of the colonoscope from the proximal end to the distal end. The wire is then secured, for example with a clamp at the distal end of the device, such that the proximal ends of the device and positioning probe are in tight association. The probe is then inserted into the colon along with the device. When the proximal tip of the probe is in the desired location in the colon, the wire is released and the probe is removed. In a preferred embodiment the device is manufactured with a wire attached to the proximal end. Also in a preferred embodiment, the device comprises an attachment site, for example a loop or hook or an equivalent thereof to which the wire is attached. In a preferred embodiment, the wire is attached to the attachment site by a connector or a knot or an equivalent thereof. The free end of the wire is then passed through the suction channel of the probe. In a more preferred embodiment, the wire is passed through the loop or hook and both ends of the wire are passed through the suction channel of the probe. One or both ends of the wire may be threaded directly through the suction channel of the probe. Alternatively, a forceps or threading device, or equivalent thereof, is inserted through the suction channel and attached to the end(s) of the wire. The forceps is then removed pulling the wire through the suction channel. The end(s) of the wire are secured during insertion of the probe to keep the proximal end of the device associated with the proximal end of the probe. When the device is in the desired position in the colon, the wire is released thus releasing the device from the probe. In one embodiment the wire is then removed prior to removing the probe. In a preferred embodiment, to prevent displacement of the device during removal of the colonoscope, a long thin forceps or snare approximately longer than twice the length of the colonoscope is inserted through the suction channel therein and clamped on the proximal end of the device. In a preferred embodiment, the proximal end of the device is adapted so as to be securely grasped by the forceps or snare. Also in a preferred embodiment, the proximal end comprises a ring or other shape that acts as a catch for the forceps or snare to be securely attached to during removal of the colonoscope. In one embodiment the snare comprises a retractable hook at its proximal end, and the colonic access device comprises a ring at its proximal tip. The hook is secured in the ring under direct observation through the colonoscope. Once the forceps or snare is securely attached to the device, the colonoscope is removed and the forceps or snare is used to keep the proximal end of the device at the desired location in the colon. The colonoscope is removed over the forceps or snare. In a preferred embodiment, the length of the forceps or snare is at least twice the length of the colonoscope. The colonoscope is then completely removed from the patient and covers the length of forceps or snare outside the patient. Thereafter, the thin forceps or snare is removed readily without displacing the device. Removal of the colonoscope or other positioning probe, preferably is performed by two people. One person removes the colonoscope while the other person holds the distal end of the device in place. This prevents the device from being dragged out with the colonoscope due to friction. Friction between the colonoscope and the device is expected to be highest close to the rectum, where the diameter of the lumen of the colon is smallest.

In other embodiments of the invention the releasable tether comprises a latch by which the device and the positioning probe are attached. The latch is activated to release the device from the positioning probe when the device is located at the desired position in the colon, cecum, or ileum. The position of the device is monitored by the practitioner using, for example, a visual display that relays information from the video chip located on the proximal tip of a colonoscope. The latch is then activated by the practitioner to release the device from the colonoscope, and the colonoscope is removed as described previously. Latches contemplated by the invention comprise mechanical latches which are activated by wires or strings, magnetic latches which are activated by an electric current, and other tethers which are activated remotely by a practitioner to release the device from the positioning probe inside the colon of a patient. In an alternative embodiment, a colonoscope is inserted conventionally, then a long guidewire is passed through the suction channel thereof. The colonoscope is then withdrawn over the guidewire, leaving the guidewire in place. Thereafter, the device is advanced over the guidewire to the desired extent and the guidewire withdrawn.

In a further embodiment, the invention comprises delivering a releasable stent to a specific position in the colon or terminal ileum. In a preferred embodiment, the stent is coiled and self-extending. The stent may be delivered attached either to a device of the invention or directly to a positioning probe such as a colonoscope. Once in the desired position, the stent is released to uncoil and expands to adopt the size of the diameter of the lumen of the ileum or colon. Stents known in the art are currently used to treat defects in the oesophagus of a patient. Stents of the invention are designed to exert sufficient pressure, when released, on the wall of the ileum or colon in order to stay in position without exerting excessive pressure that could damage the ileum or colon. In a preferred embodiment, a stent of the invention is adapted to adopt a size that is appropriate for the location at which the stent is to be placed. In a preferred embodiment, the stent is positioned by monitoring its location under direct observation through a colonoscope. Alternatively, the position of the stent in the ileum is observed by X-ray analysis, in the presence of contrast agent in the ileum.

In one embodiment, the stent is useful to help heal fistulas in the mucosal epithelium of the ileum or colon. The stent is placed such that its surface is in direct contact with the opening of the fistula, thus effectively sealing it off from the gastrointestinal lumen. The fistula heals more rapidly when it is not exposed to the gastrointestinal contents.

In an alternative embodiment, the stent is useful to enlarge or stabilize a narrowing or stricture of the ileum or colon. A narrowing or stricture can be caused by infections, tumors, fistulas, inflammation of the mucosal epithelium or underlying tissue, and other bowel diseases.

Alternatively, the stent is useful as an anchored drug delivery device. In a preferred embodiment, the stent comprises a drug delivery chamber. In a most preferred embodiment the drug delivery chamber is adapted for slow drug release. Various methods for slow drug release are known in the art, including gas driven release and slow release polymers. The chamber is either an integral part of the stent or alternatively is connected to the stent via an attachment. The attachment is preferably flexible, so that the device does not obstruct the lumen of the colon or ileum. The drug delivery chamber is preferably shaped to minimize resistance to the flow of gastrointestinal contents. A preferred shape is elongated and ovoid. In a preferred embodiment, the drug delivery chamber comprises a reservoir that can be replenished. The reservoir can be refilled by injecting the drug through a port in the chamber wall using a needle (for example a sclerotherapy needle) under direct observation through a colonoscope. In an alternative embodiment, the drug delivery chamber is replaceable. The attachment connecting the chamber to the stent is releasable so that the chamber can be removed and replaced with a new or different chamber. A slow release drug delivery device according to the invention is useful to provide constant drug delivery to the ileum, cecum, or colon, thus avoiding unnecessary (and possibly undesirable) absorption of the drug in the proximal small bowel associated with oral drug administration. Methods and devices of the invention are particularly useful to treat a patient suffering from Crohn's disease, especially after surgical resection of the ileum or colon. Using methods and devices of the invention, a drug delivery chamber attached to a stent is placed at or adjacent the site of anastomosis. The slow and constant delivery of drugs (for example steroids or anti-inflammatory compounds) to the site of anastomosis helps prevent the recurrence of Crohn's disease related lesions following surgical intervention.

Other features of the invention will become apparent upon consideration of the foregoing description. Accordingly, the invention is limited only by the scope of the appended claims.

I claim:

1. A colonic access device comprising:
   a flexible tubular member having a distal end and a proximal end; and,
   a tether at said proximal end of said tubular member for releasable association of said tubular member with a positioning probe,
   wherein said tether attaches said proximal end of said flexible tubular member to said positioning probe for insertion of said flexible tubular member in association with said positioning probe into a patient's colon, and wherein release of said tether releases said flexible tubular member from said positioning probe thereby to allow removal of said positioning probe without removing said flexible tubular member from the colon of said patient.

2. The device of claim 1, wherein said positioning probe is a colonoscope.

3. The device of claim 1, wherein said tubular member defines a hollow cavity.

4. The device of claim 3, wherein said hollow cavity is in communication with an outside environment via a proximal opening and a distal opening.

5. The device of claim 4 wherein said openings are recessed in an external wall of said tubular member.

6. The device of claim 3 wherein said tubular member further defines a plurality of openings disposed along the length of said member, and wherein each member of said plurality is in communication with an independent channel disposed inside said internal cavity.

7. The device of claim 1 further comprising a plurality of protrusions extending from said member and serving to separate said member from the colonic epithelium.

8. The device of claim 7 wherein said protrusions are inflatable.

9. The device of claim 8 wherein at least a portion of said member is inflatable.

10. The device of claim 1 further comprising pressure sensors in association with said tubular member.

11. The device of claim 1 wherein said proximal end is tapered.

12. The device of claim 1 wherein at least said proximal end is shaped to conform to the contour of said colonoscope.

13. The device of claim 1 wherein said tether is a bore at said proximal end.

14. The device of claim 1 wherein said tether is a latch.

15. A method for placing a colonic access device into a patient's colon, comprising the steps of:
   a) inserting into a patient's colon a positioning probe in releasable association with a colonic access device, wherein said colonic access device comprises:
      a flexible tubular member having a distal end and a proximal end; and, a tether at said proximal end of said tubular member for releasable association of said tubular member with said positioning probe, wherein said tether attaches said proximal end of said flexible tubular member to said positioning probe for insertion of said flexible tubular member in association with said positioning probe into the patient's colon;

b) releasing said access device from said positioning probe; and c) removing said positioning probe from said patient's colon.

16. The method of claim 15 wherein said removing step comprises grasping said device with a snare.

17. A method for monitoring a colorectal disorder, comprising the steps of:

a) inserting into a patient's colon a positioning probe in releasable association with a colonic access device, wherein said colonic access device comprises:

a flexible tubular member having a distal end and a proximal end; and, a tether at said proximal end of said tubular member for releasable association of said tubular member with said positioning probe, wherein said tether attaches said proximal end of said flexible tubular member to said positioning probe for insertion of said flexible tubular member in association with said positioning probe into the patient's colon;

b) releasing said access device from said positioning probe;

c) removing said positioning probe from said patient's colon; and d) obtaining colonic effluent via said access device.

18. The method of claim 17 wherein said colonic effluent is analyzed for the presence of blood.

19. A method for treating a colorectal disorder, comprising the steps of:

a) inserting into a patient's colon a positioning probe in releasable association with a colonic access device, wherein said colonic access device comprises:

a flexible tubular member having a distal end and a proximal end; and, a tether at said proximal end of said tubular member for releasable association of said tubular member with said positioning probe, wherein said tether attaches said proximal end of said flexible tubular member to said positioning probe for insertion of said flexible tubular member in association with said positioning probe into the patient's colon;

b) releasing said access device from said positioning probe;

c) removing said positioning probe from said patient's colon; and d) providing a pharmaceutical composition via said access device.

20. A method for treating a colorectal disorder, comprising the steps of:

a) inserting into a patient's colon a positioning probe in releasable association with a colonic access device, wherein said colonic access device comprises:

a flexible tubular member having a distal end and a proximal end; and, a tether at said proximal end of said tubular member for releasable association of said tubular member with said positioning probe, wherein said tether attaches said proximal end of said flexible tubular member to said positioning probe for insertion of said flexible tubular member in association with said positioning probe into the patient's colon;

b) releasing said access device from said positioning probe;

c) removing said positioning probe from said patient's colon; and d) decompressing an external environment via said access device.

21. The method according to claim 20 wherein said colorectal disorder is selected from the group consisting of Ogilvie's syndrome and colonic pseudo-obstruction.

22. A method for radiographically visualizing the small intestine of a patient comprising the steps of:

a) inserting into a patient's colon a positioning probe in releasable association with a colonic access device, wherein said colonic access device comprises:

a flexible tubular member having a distal end and a proximal end; and, a tether at said proximal end of said tubular member for releasable association of said tubular member with said positioning probe, wherein said tether attaches said proximal end of said flexible tubular member to said positioning probe for insertion of said flexible tubular member in association with said positioning probe into the patient's colon;

b) releasing said access device from said positioning probe;

c) removing said positioning probe from said patient's colon; and d) delivering a radiologic contrast agent via said device.

23. The method of claim 22 wherein said contrast agent is selected from the group consisting of barium and gastrografin.

24. A colonic access device comprising:

a flexible tubular member of between about 5 feet and about 8 feet in length, having a proximal end and a distal end; and a tether at said proximal end of said tubular member for releasable association of said tubular member with a positioning probe, wherein said tether attaches said proximal end of said flexible tubular member to said positioning probe for insertion of said flexible tubular member in association with said positioning probe into a patient's colon, and wherein release of said tether releases said flexible tubular member from said positioning probe thereby to allow removal of said positioning probe without removing said flexible tubular member from the colon of said patient.

25. The colonic access device of claim 24, wherein said length is about 6 feet.

* * * * *